US011999686B2

(12) United States Patent
Niessner et al.

(10) Patent No.: US 11,999,686 B2
(45) Date of Patent: Jun. 4, 2024

(54) PROCESS FOR DE-POLYMERIZATION OF STYRENIC MONOMER-CONTAINING POLYMERS AND FOR RETRIEVAL OF STYRENIC MONOMERS

(71) Applicant: INEOS STYROLUTION GROUP GMBH, Frankfurt am Main (DE)

(72) Inventors: Norbert Niessner, Friedelsheim (DE); Bianca Wilhelmus, Hanau (DE); Hannes Kerschbaumer, Bad Soden am Taunus (DE); Michiel Verswyvel, Mechelen (BE); Petra Inghelbrecht, Laarne Kalken (BE); Thomas W. Cochran, Channahon, IL (US); KyungHo Shon, Yongin (KR); Mohammed Abboud, Riverside, IL (US); Ricardo Cuetos, Naperville, IL (US); Hans-Dieter Schwaben, Rhodt (DE); Jens Kathmann, Worb/Bern (CH); Thad Urquhart, Seabrook, TX (US); Timothy A. Brown, League City, TX (US); Tim Wong, League City, TX (US); Walter De Vet, BJ Gilze (NL); Hans-Werner Schmidt, Bayreuth (DE); Andreas Schedl, Bayreuth (DE); Tristan Kolb, Bayreuth (DE)

(73) Assignee: INEOS STYROLUTION GROUP GMBH, Frankfurt am Main (DE)

( * ) Notice: Subject to any disclaimer, the term of this patent is extended or adjusted under 35 U.S.C. 154(b) by 510 days.

(21) Appl. No.: 17/419,063

(22) PCT Filed: Jan. 7, 2020

(86) PCT No.: PCT/EP2020/050185
§ 371 (c)(1),
(2) Date: Jun. 28, 2021

(87) PCT Pub. No.: WO2020/144165
PCT Pub. Date: Jul. 16, 2020

(65) Prior Publication Data
US 2022/0081372 A1 Mar. 17, 2022

(30) Foreign Application Priority Data

Jan. 7, 2019 (EP) .................................. 19150515

(51) Int. Cl.
*C07C 4/22* (2006.01)
*B01D 3/14* (2006.01)
(Continued)

(52) U.S. Cl.
CPC ................ *C07C 4/22* (2013.01); *B01D 3/143* (2013.01); *B01D 3/4227* (2013.01); *C07C 7/04* (2013.01);
(Continued)

(58) Field of Classification Search
CPC .. C07C 4/22; C07C 7/04; C07C 15/46; B01D 3/4227; C08J 11/12; C08J 2325/06;
(Continued)

(56) References Cited

U.S. PATENT DOCUMENTS 2,457,361 A 12/1948 Gadwa
3,763,015 A 10/1973 Morimoto et al.
(Continued)

FOREIGN PATENT DOCUMENTS

CN 104744206 A 7/2015
JP H0585964 A 4/1993
(Continued)

OTHER PUBLICATIONS

Grause et al., "Feedstock recycling of waste polymeric material", Journal of Material Cycles and Waste Management, 2011, 265-282, 13(4), Springer.
(Continued)

*Primary Examiner* — Thuan D Dang
(74) *Attorney, Agent, or Firm* — RAPHAEL BELLUM PLLC; Aaron M. Raphael

(57) ABSTRACT

The invention relates to an improved process for providing purified styrenic monomers, such as styrene, from styrene-containing polymer waste. Styrene-containing waste is
(Continued)

depolymerized in a suitable reactor, and the depolymerization products are condensed and separated in a three-step distillation process.

20 Claims, 1 Drawing Sheet

(51) Int. Cl.
  *B01D 3/42* (2006.01)
  *C07C 7/04* (2006.01)
  *C08J 11/12* (2006.01)
  *C10B 53/07* (2006.01)
(52) U.S. Cl.
  CPC ............... *C08J 11/12* (2013.01); *C10B 53/07* (2013.01); *C08J 2325/06* (2013.01)
(58) Field of Classification Search
  CPC ......... C10B 53/07; C10B 7/10; C10B 20/143; Y02W 30/62; C08F 8/50
  See application file for complete search history.

(56) References Cited

U.S. PATENT DOCUMENTS

| | | |
|---|---|---|
| 4,959,128 A | 9/1990 | Berg |
| 5,072,068 A | 12/1991 | Luo et al. |
| 6,018,085 A | 1/2000 | Ponsford et al. |
| 2021/0277202 A1 | 9/2021 | Wilhelmus et al. |

FOREIGN PATENT DOCUMENTS

| | | |
|---|---|---|
| JP | 2000191825 A1 | 7/2000 |
| JP | 2005/132802 A | 5/2005 |
| WO | 2018/224482 A1 | 12/2018 |

OTHER PUBLICATIONS

Bouster et al., "Study of the pyrolysis of polystyrenes: Kinetics of thermal decomposition", Journal of Analytical and Applied Pyrolysis, 1980, 297-313, 1, Elsevier Scientific Publishing Company, Amsterdam, The Netherlands.

Bouster et al., "Evolution of the product yield with temperature and molecular weight in the pyrolysis of polystyrene", Journal of Analytical and Applied Pyrolysis, 1989, 249-259, 15, Elsevier Science Publishers V.B., Amsterdam, The Netherlands.

Achilias et al., "Chemical recycling of polystyrene by pyrolysis: Potential use of the liquid product for the reproduction of polymer", Macromolecular Materials and Engineering, 2007, 923-934, 292(8), Wiley, Weinheim, Germany.

Baskaran et al., "Anionic Vinyl Polymerization", , Controlled and Living Polymerizations: From Mechanisms to Applications, 2009, 1-56, Wiley, Weinheim, Germany.

Brebu et al.,"The individual and cumulative effect of brominated flame retardant and polyvinylchloride (PVC) on thermal degradation of acrylonitrile-butadiene-styrene (ABS) copolymer", Chemosphere, 2004, 433-440, 56(5), Elsevier.

International Preliminary Report on Patentability in International Application No. PCT/EP2020/050185, dated Jul. 1, 2020.

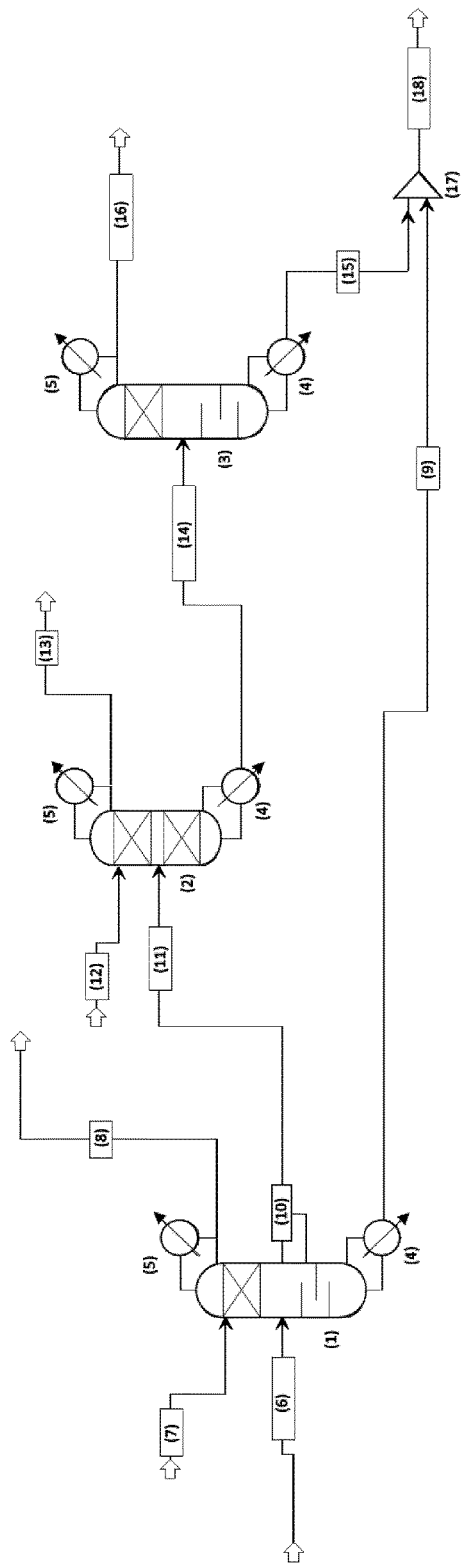

PROCESS FOR DE-POLYMERIZATION OF STYRENIC MONOMER-CONTAINING POLYMERS AND FOR RETRIEVAL OF STYRENIC MONOMERS

A process is provided for the de-polymerization of styrene-containing polymers and a method for separation of styrenic monomers from reaction products obtained by the depolymerization of a polymer waste that contains styrene.

Climate change, environmental pollution, population growth and resource dependency trigger the ecological and economic necessity of the transition from a linear to a circular economy. Since the 1990s, intensive efforts were made to develop processes for the recovery of raw materials from recycling of plastic waste. These efforts have not yet resulted in large-scale applications, in particular due to unresolved process engineering problems and economic reasons, such as the non-availability of suitable materials. However, the topic of plastic waste as well as a greater ecological awareness and a need for sustainable solutions have led to a growing interest in chemical recycling.

Not all thermoplastic polymers are equally suited for chemical recycling. The thermal decomposition of polyolefins or polyesters results in mixtures of waxes, light oil and gases. The degradation of polyethylene terephthalate (PET) results in organic acids, mainly benzoic acid and terephthalic acid, which are corrosive and may also cause clogging of the reactor (G. Grause et al., Feedstock recycling of waste polymeric material, in: Journal of Material Cycles and Waste Management, 13(4), 2011, 265-282).

In the case of polystyrene and other styrene-containing polymers, it is possible to depolymerize these polymers into their basic components, especially styrenic monomers, which make polystyrene and other styrenic monomer-containing polymers excellent choices for chemical recycling. However, the resulting product mixture of a depolymerization process needs to be purified in order to use the components as raw material for new purposes, such as polymerization processes.

If polystyrene is sufficiently thermally treated, it decomposes to styrene monomers, but incomplete decomposition also results in the formation of e.g. styrene dimers, trimers and other oligomers. If the decomposition conditions are too strong, side products, e.g. benzene, toluene, ethylbenzene, cumene and alpha-methyl styrene, may be formed. The amounts of these reaction products vary and depend on the reaction conditions and on the raw materials that have been used (see C. Bouster et al., Study of the pyrolysis of polystyrenes: Kinetics of thermal decomposition, Journal of Analytical and Applied Pyrolysis, 1 (1980) 297-313 and C. Bouster et al., Evolution of the product yield with temperature and molecular weight in the pyrolysis of polystyrene, in: Journal of Analytical and Applied Pyrolysis 15 (1989) 249-259).

Styrenic monomers can be used, e.g. for a new polymerization process. Styrenic oligomers may disturb the polymerization process, as they influence, even in small quantities, important properties of the polymer. This is similar for other side products as well. Therefore, the styrenic monomers have to be separated from other components of the product mix, to ensure a high product quality.

Especially aromatic compounds other than styrenic monomers can act as chain transfer agents in radical-based polymerization processes, lowering the average molecular weight of the polymers produced and contributing to polymers with a lower glass transition temperature, Tg (D. S. Achilias et al., Chemical recycling of polystyrene by pyrolysis: Potential use of the liquid product for the reproduction of polymer, in: Macromolecular Materials and Engineering, 292(8) (2007) 923-934). Acidic protons from e.g. carboxylic acid, alcohols, aldehydes or ketones act as terminating agent in anionic polymerization processes of styrene (D. Baskaran et al., Anionic Vinyl Polymerization, in: Controlled and Living Polymerizations: From Mechanisms to Applications, John Wiley & Sons, 2009, 1-56).

Polystyrene product waste often also contains one or several additives, like brominated flame retardants, such as polybrominated biphenyls, polybrominated diphenyl oxides, tetrabromo bisphenol-A or polybrominated epoxy resins, which need to be removed in order to generate styrenic monomers that may be used for high-quality products and special purposes, such as polystyrene for food packaging.

Bromine from flame retardants may lead to acidic or toxic gases such as HBr during thermal decomposition and can also form organic compounds in the pyrolysis oil (M. Brebu et al., The individual and cumulative effect of brominated flame retardant and polyvinylchloride (PVC) on thermal degradation of acrylonitrile-butadiene-styrene (ABS) copolymer, in: Chemosphere, 56(5) (2004) 433-440). Therefore it seems advantageous to remove unwanted compounds from the styrenic monomers that have been obtained in the recycling process.

Typically, in the industrial scale, styrene is produced from ethylbenzene by dehydrogenation (D. James et al., Styrene, in: Ullmann's Encyclopedia of Industrial Chemistry, 34, Wiley (2012) 529-544). However, the crude styrene formed in this process contains only small amounts of so called "heavy boilers" (defined as molecules that have a boiling point higher than styrene).

A typical crude styrene composition is shown in Table 1.

TABLE 1

Typical crude styrene composition from the ethylbenzene dehydrogenation process for the production of styrene:

| Component | Boiling point [° C.] | Content [weight-%] |
| --- | --- | --- |
| Benzene | 80 | 1 |
| Toluene | 110 | 2 |
| Ethylbenzene | 136 | 32 |
| Styrene | 145 | 64 |
| Others | >145 | 1 |

The common purification procedure for styrene from this reaction mixture is described by D. James et al. in Ullmann's Encyclopedia of Industrial Chemistry, 34, Wiley (2012) 529-544 that in the first step, benzene and toluene are removed, in the second step, ethylbenzene is separated and recycled back into the process and the third step comprises a vacuum distillation to separate styrene from the heavy boilers.

A similar process is described in U.S. Pat. No. 2,457,361 (Lummus). In a series of distillation columns, first the low boilers are separated from the mixture then after several other separation steps, finally the heavy boilers are removed and pure styrene is collected.

The separation of styrene from ethylbenzene by extractive distillation is described e.g. in U.S. Pat. No. 4,959,128 (Berg). However, this teaching is only related to the separation of ethylbenzene and styrene and does not provide a solution for the separation of styrene from a reaction mixture with a high amount of heavy boilers.

The separation of styrene from thermally cracked crude oil by extractive distillation is also described in U.S. Pat. No.

3,763,015 (Toray). However, also in this process, the mixture containing styrene to be separated is rich in light boilers and poor in heavy boilers and poor in styrene as well. A comparable process is described in CN-A 104744206, where in a method for extractive distillation of styrene from a pyrolysis gasoline C8 fraction the heavy boilers are removed in the last process step.

In JP-A 2005132802 and JPH11100875 (Toshiba Plant Systems), a process to recover styrene from waste polystyrene is described, but no solution for the separation of light boilers, styrene and heavy boilers is provided.

WO 2018/224482 (Ineos Styrolution Group) discloses a method for pyrolytic depolymerization of styrene-containing plastic waste, generating low-molecular components for further processing. JP2000191825 (San Kaihatsu) teaches a method for recovering styrenic monomers from polystyrene waste, but provides no solution for the separation of ethylbenzene from styrenic monomers. U.S. Pat. No. 5,072,068 (Guangdong International) describes a method to recover styrenic monomers from discarded polystyrene, but does not provide a solution for the purification of styrenic monomers to a quality suitable for re-polymerization.

However, when styrene is formed by de-polymerization of polystyrene or other styrene-containing polymers, the reaction mixture has a different composition than the crude styrene from the industrial ethylbenzene process.

Although the styrenic monomer content might be similar, the amount of ethylbenzene and other "light boilers" (defined as molecules that have a boiling point lower than styrene) is much smaller in the reaction mixture from the recycling process, and the amount of heavy boilers, especially styrene oligomers, is much higher. A typical yield composition is given in Table 2 (D. S. Achilias et al., Chemical recycling of polystyrene by pyrolysis: potential use of the liquid product for the reproduction of polymer, Macromol. Mater. Eng. 292, (2007), 923-934). In addition to that, the reaction mixture from recycled polystyrene may also contain various other additives and their decomposition products and products from side reactions, such as brominated flame retardants, butadiene and the like.

TABLE 2

Typical yield in de-polymerization with polystyrene

| Component | Boiling point [° C.] | Content [weight-%] |
|---|---|---|
| Toluene | 110 | 2.0 |
| Ethylbenzene | 136 | 0.5 |
| Styrene | 145 | 63.9 |
| Alpha methyl styrene | 166 | 2.1 |
| 2,4-Diphenyl-1-butene (styrene dimer) | 298 | 14.0 |
| 2,4,6-Triphenyl-1-hexene (styrene trimer) | 448 | 2.2 |
| other aromatic compounds | >145 | 15.3 |

Therefore, the established purification processes for crude styrene from the ethylbenzene process as described above are not sufficient to provide styrenic monomers from the de-polymerization process of polystyrene or other styrene-containing polymers that are suitable for producing high-quality polystyrene (or other styrene-polymers) again, because different compounds are present in the reaction mixture and also the quantities of the compounds are not the same as in the crude styrene from the ethylbenzene process. There is a high demand for a purification process that provides styrenic monomers with high purity from polystyrene waste.

It is one task of this invention to provide styrenic monomers with a sufficient purity for a polymerization process that then provides polymers, such as e.g. polystyrene, with high and constant quality, and without unwanted compounds, such as halogenated flame retardants and their decomposition products.

One further objective of the present invention is to provide a styrene composition that contains styrene of high purity and a process for its preparation (or separation).

This objective is achieved by a process for retrieving styrenic monomers from a polymer mixture (P), the polymer mixture (P) comprising:
(A) 1 wt-% to 99.8 wt-%, related to the total weight of polymer mixture (P), of a styrenic polymer comprising:
i. 70 wt-% to 100 wt-%, related to the total weight of (A), of repeating units derived from a styrenic monomer selected from styrene and alpha-methylstyrene;
ii. 0 wt-% to 30 wt-%, often 0 wt-% to 15 wt-%, related to the total weight of (A), of repeating units derived from dienes;
iii. 0 wt-% to 2 wt-%, related to the total weight of (A), of repeating units derived from other radically co-polymerizable monomers;
(B) 0.1 wt-% to 98.9 wt-%, related to the total weight of polymer mixture (P), of a mixture of polymers other than polymer (A);
(C) 0.1 wt-% to 30 wt-%, related to the total weight of polymer mixture (P), of organic or inorganic polymer additives and auxiliaries; and optionally
(D) 0 wt-% to 50 wt-%, related to the total weight of polymer mixture (P), of impurities such as, but not limited to, food waste, dirt, packaging residues or moisture,
the process comprising the steps of:
I) feeding the polymer mixture (P) into a pyrolysis zone of a pyrolysis reactor and subjecting it to a temperature of 300° C. to 650° C., in particular of 300° C. to 550° C., measured as the average temperature of the polymer mixture (P) at the inner surface of the reactor wall during the reaction runtime, during which at least partial decomposition of the component (A) to styrenic monomers takes place, and a gas containing said styrenic monomers is formed;
II) condensing the condensable substances, including styrenic monomers, from the gas formed in step I) at a cooling rate of more than 500 K/min;
III) optionally, fractionating the condensed substances from step II) in a distillation column (X).

The process described typically provides styrenic monomers with a purity of at least 40 wt-%, preferably at least 90 wt-%, more preferably at least 98 wt-%, more preferably 99.8 wt-%, and allows for a new polymerization of the styrenic monomers to e.g. polystyrene with sufficient quality for various commercial applications. In this process, the polymer mixture (P) is subject to a pyrolysis in a pyrolysis reactor at a temperature of 300° C. to 650° C., in particular of 300° C. to 550° C., measured as the average temperature of the polymer mixture at the inner surface of the reactor wall during the reaction.

Styrene-Containing Polymer Mixture (P)

As a starting material for the process of this invention, a suitable styrene-containing polymer mixture (P) comprises and preferably consists of the components (A), (B), (C), and optionally (D):
(A) 1 wt-% to 99.8 wt-%, preferably 40 wt-% to 99.8 wt-%, more preferably 60 wt-% to 99.8 wt-%, most preferably 80 wt-% to 99.8 wt-%, related to the total weight of polymer mixture (P), of a styrenic polymer;

(B) 0.1 wt-% to 98.9 wt-%, preferably 0.1 wt-% to 40 wt-%, more preferably 0.1 wt-% to 30 wt-%, most preferably 0.1 wt-% to 19.9 wt-%, related to the total weight of polymer mixture (P), of a mixture of polymers other than polymer (A);

(C) 0.1 wt-% to 30 wt-%, preferably 0.1 wt-% to 20 wt-%, more preferably 0.1 wt-% to 10 wt-%, most preferably 0.1 wt-% to 5 wt-%, related to the total weight of polymer mixture (P), of organic or inorganic polymer additives;

(D) 0 wt-% to 50 wt-%, preferably 0 wt-% to 30 wt-%, more preferably 0 wt-% to 15 wt-%, most preferably 0 wt-% to 5 wt-% related to the total weight of polymer mixture (P), of impurities such as, but not limited to, food waste, dirt, packaging residues or moisture.

The polymer mixture (P) can contain or originate from industrial or post-consumer waste. The industrial or post-consumer waste can be collected via the normal waste collection systems, e.g. at companies, public institutions and families. It can also contain waste that was collected e.g. from nature, e.g. marine areas, seas, coasts, rivers, lakes, fields, forests, and others.

Component (A):

The polymer mixture (P) comprises, as component (A), a styrenic polymer comprising:

i. 70 wt-% to 100 wt-%, preferably 85 wt-% to 100 wt-%, more preferably 95 wt-% to 100 wt-%, related to the total weight of (A), of repeating units derived from a styrenic monomer selected from styrene and alpha-methylstyrene, preferably styrene;

ii. 0 wt-% to 30 wt-%, preferably 0 wt-% to 15 wt-%, more preferably 0 wt-% to 5 wt-%, related to the total weight of (A), of repeating units derived from dienes, preferably butadiene;

iii. 0 wt-% to 2 wt-%, preferably 0 wt-% to 1 wt-%, more preferably 0 wt-% to 0.5 wt-%, related to the total weight of (A), of repeating units derived from other radically copolymerizable monomers, which are preferably selected form the group consisting of acrylonitrile, vinyl chloride, methyl methacrylate, t-butyl methacrylate, isoprene, maleic anhydride and phenylmaleimide.

Thus, component (A) may be but is not limited to styrene-based polymers such as general purpose polystyrenes (not impact modified) or impact modified polystyrenes, vinylaromatic copolymers such as styrene acrylonitrile copolymers, alpha methyl styrene acrylonitrile copolymers, styrene maleic anhydride copolymers, styrene phenylmaleimide copolymers, styrene methyl methacrylate copolymers, styrene acrylonitrile maleic anhydride copolymers, styrene acrylonitrile phenylmaleimide copolymers, alpha methyl styrene acrylonitrile methyl methacrylate copolymers, alpha methyl styrene acrylonitrile t-butyl methacrylate copolymers, styrene butadiene copolymers, styrene isoprene copolymers and styrene acrylonitrile t-butyl methacrylate copolymers. Most preferably, component (A) is a general purpose (not impact modified) polystyrene.

Processes for producing these polymers are known to the person skilled in the art and are described in the literature.

Component (B):

The polymer mixture (P) comprises, as component (B), a mixture of one or more polymers other than styrenic polymer (A). These polymers are preferably selected from the group consisting of: polyolefins; hydrogenated or non-hydrogenated ethylenepropylene-diene-rubber (EPDM); polyvinyl chloride (PVC); chlorinated polyvinyl chloride (c-PVC); polycarbonates; polyamides; and polyesters.

In a particularly preferred embodiment, component (B) contains iv. 0 wt-% to 1 wt-%, preferably 0 wt-% to 0.8 wt-%, related to the total weight of (B), of PVC or c-PVC;

v. 0 wt-% to 35 wt-%, preferably 0 wt-% to 25 wt-%, more preferably 0 wt-% to 15 wt-%, related to the total weight of (B), of polyethylenes or polypropylenes or (hydrogenated or non-hydrogenated) EPDM;

vi. 0 wt-% to 10 wt-%, preferably 0 wt-% to 7 wt-%, related to the total weight of (B), of (hydrogenated or non-hydrogenated) styrene-butadiene copolymers comprising at least 15 wt-% butadiene based on the total weight of styrene-butadiene copolymer;

vii. 0 wt-% to 5 wt-%, preferably 0 wt-% to 3 wt-%, related to the total weight of (B), of polyesters or polycarbonates or polyamides, provided that the amounts of components selected from groups iv., v., vi. and vii. sum up to at least 0.1 wt-%, related to the total weight of polymer mixture (P).

Component (C):

The polymer mixture (P) comprises, as component (C), organic or inorganic polymer additives. These organic or inorganic polymer additives are preferably selected from the group consisting of halogenated substances, inorganic or organic dyes or pigments, lubricants, waxes, amides of long chain organic acids, emulsifiers, soaps, paper, cardboard, metals, metal oxides, metal salts, other fillers, and other additives such as UV stabilizers, hindered amine light stabilizers (HALS), hindered phenols, disulfite stabilizers, quenchers and absorbers. In one embodiment, (C) also can be water.

In a particularly preferred embodiment, component (C) contains:

viii. 0 wt-% to 10 wt-%, preferably 0 wt-% to 5 wt-%, related to the total weight of (P), of water;

ix. 0 wt-% to 1 wt-%, preferably 0 wt-% to 0.5 wt-%, related to the total weight of (P), of halogenated substances such as halogenated flame retardants;

x. 0 wt-% to 10 wt-%, preferably 0 wt-% to 5 wt-%, more preferably 0 wt-% to 3 wt %, related to the total weight of (P), of inorganic and/or organic dyes and/or pigments such as carbon black or titanium dioxide;

xi. 0 wt-% to 10 wt-%, preferably 0 wt-% to 5 wt-%, related to the total weight of (P), of lubricants or waxes such as paraffin or paraffin wax or amides of long chain organic acids;

xii. 0 wt-% to 5 wt-%, preferably 0 wt-% to 3 wt-%, related to the total weight of (P), of emulsifiers or soaps such as polyalkylene oxides, sodium docecyl sulfonate or potassium stearate;

xiii. 0 wt-% to 5 wt-%, preferably 0 wt-% to 3 wt-%, related to the total weight of (P), of paper or cardboard;

xiv. 0 wt-% to 1 wt-%, preferably 0 wt-% to 0.5 wt-%, related to the total weight of (P), of metals or metal oxides or metal salts;

xv. 0 wt-% to 10 wt-%, preferably 0 wt-% to 5 wt-% related to the total weight of (P), more preferably 0 wt-% to 1 wt-% of further fillers, such as glass fibers, clays, ceramic particles, carbon fibers, potassium titanate whiskers, aramid fibers, and particularly preferably glass fibers;

xvi. 0 wt-% to 2 wt-%, preferably 0 wt-% to 1 wt-% related to the total weight of (P), of other additives such as heat stabilizers, oxidation retarders, UV stabilizers, HALS, hindered phenols, disulfite stabilizers, quenchers or absorbers, provided that the amount of components selected from groups viii., ix., x., xi., xii., xiii., xiv., xv. and xvi. sums up to at least 0.1 wt-%, related to the total weight of polymer mixture (P).

Further components (C) may be mold-release agents, dyes, fillers and reinforcing agents and plasticizers and combinations of two or more of such additives or auxiliaries.

Examples of oxidation retarders and heat stabilizers are halides of metals of group I of the Periodic Table of the Elements, e.g. sodium halides, potassium halides, and lithium halides. It is also possible to use zinc fluoride and zinc chloride. It is also possible to use sterically hindered phenols, hydroquinones, substituted members of that group, secondary aromatic amines, if appropriate in conjunction with phosphorus-containing acids or salts of these, and mixtures of said compounds, preferably at concentrations of up to 1 wt-%, related to the total weight of (P).

Examples of UV stabilizers are various substituted resorcinols, salicylates, benzotriazoles, and benzophenones, the amounts generally used of these being up to 2 wt-%, related to the total weight of (P).

As a component (C), the polymer mixture (P) may also contain flame retardants based on phosphorus compounds.

Examples of lubricants and mold-release agents, usually present in quantities up to 1 wt-%, related to the total weight of (P), are stearic acid, stearyl alcohol, alkyl stearates, and stearamides, and also esters of pentaerythritol with long-chain fatty acids. It is also possible to use stearates of calcium, of zinc, or of aluminum, and also dialkyl ketones, e.g. distearyl ketone.

Examples for pigments and dyes are organic pigments and dyes such as, but not limited to, azo, naphthol, phthalocyanine, dioxazine, anthraquinone and diketopyrrolopyrrole pigments, and inorganic pigments such as, but not limited to, titanium dioxide, rutile yellow, cobalt blue, ultramarine blue, chrome oxide green, iron oxide and carbon black.

Examples of fillers in component (C) are fibers or particulate fillers. Preferred fibrous fillers or fibrous reinforcing materials are carbon fibers, potassium titanate whiskers, aramid fibers, and particularly preferably glass fibers. If glass fibers are used, these can have been equipped with size and with an adhesion promoter, to improve compatibility with the matrix material. The diameter of the carbon fibers and glass fibers used is generally in the range from 6 to 20 µm.

The glass fibers can be incorporated either in the form of short glass fibers or else in the form of long glass fibers or continuous-filament strands, and also by way of example in the form of what are known as rovings. The average length of the glass fibers in the finished injection molding is preferably in the range from 0.08 to 0.5 mm. Carbon fibers or glass fibers can also be used in the form of textiles, mats, or glass silk rovings. Suitable particulate fillers are amorphous silica, magnesium carbonate (chalk), powdered quartz, mica, talc, feldspar, glass beads, and in particular calcium silicates, such as wollastonite, and kaolin, particularly calcined kaolin.

Examples for plasticizers are dioctyl phthalate, dibenzyl phthalate, butylbenzyl phthalate, hydrocarbons, n-butylbenzenesulfonamide and o- or p-toluene-ethylsulfonamide.

Component (D):

The polymer mixture (P) often comprises, as component (D), 0 wt-% to 50 wt-%, more often 0.5 to 40 wt-%, related to the total weight of polymer mixture (P), of impurities such as, but not limited to, food waste, dirt or packaging residues.

The polymer mixture (P) is depolymerized and purified in a process, preferably comprising the following steps I) to V).

Preferably at least one of the optional steps III) and V) is carried out during the process. More preferably, both optional steps III) and V) are carried out.

Step I)

In step I) of the process, the polymer mixture (P) is decomposed, in a suitable reactor by applying thermal energy, and if appropriate, shear force and/or pressure. This is done by feeding the polymer mixture (P) into the pyrolysis zone of the reactor and subjecting it to a temperature of 300° C. to 650° C., in particular 300° C. to 550° C., preferably 300° C. to 500° C., more preferably 350° C. to 450° C., measured as the average temperature of the polymer waste at the inner surface of the reactor wall during the reaction runtime, preferably with a residence time of the polymer mixture (P) in the pyrolysis zone of 0.1 to 60 minutes, more preferably 1 to 45 minutes, most preferably 2 to 30 minutes, during which at least partial decomposition of the component (A) of the polymer mixture (P) to styrenic monomers and optionally styrenic oligomers takes place, and a gas containing said styrenic monomers and optionally styrenic oligomers is formed.

Suitable reactors are for example twin screw extruders, fluidized bed reactors, stirred tank reactors (e.g. CSTR) and microwave reactors. Various reactors for applying thermal energy to a reaction mass are known to the person skilled in the art and are described in the literature.

The application of thermal energy can be done e.g. by heating and/or by radiation with microwaves. The decomposition reactor may be optionally equipped with one or more catalysts.

In one embodiment of the invention, the polymer mixture (P) is subjected to shear force and thermal energy.

In another embodiment of the invention, the polymer mixture (P) is subjected to pressure and thermal energy.

In a further embodiment of the invention, the polymer mixture (P) is subjected to shear force and pressure and thermal energy.

Step II)

In step II), the condensable substances, including styrenic monomers from the gas formed in step I) are condensed in a suitable trap. The condensable substances are thereby already separated from some highly volatile decomposition gases. The condensation takes place at a cooling rate of more than 500 K/min, preferably more than 1000 K/min.

During the condensation step II) it is advisable to add a stabilizer and/or a radical scavenger into the condensable substances. Preferably, the stabilizer and/or radical scavenger is introduced shortly before or shortly after the condensation takes place.

Suitable traps for condensing the condensable substances are known to the person skilled in the art and are described in the literature.

Optional Step III)

Optionally, in step III), the condensed vapor from step II) is fractionated in a distillation column (X). The condensed substances from step II) typically consist of styrenic monomers, ethylbenzene, and a small amount of light boilers as well as a large amount of heavy boilers. The light boilers, among others, typically contain benzene and toluene. The heavy boilers, among others, typically contain styrenic dimers and styrenic trimers.

The fractionation may be carried out in a distillation column (X), preferably with trays, providing preferably at least 3, more preferably at least 4, most preferably at least 5 theoretical stages below the feed and preferably at least 15, more preferably at least 17, most preferably at least 20 theoretical stages above the feed. In a particularly preferred embodiment, the distillation column (X) comprises 20 to 40 theoretical stages. Fractionation is described e.g. by E. Krell in "Einfuhrung in die Trennverfahren" (VEB Deutscher Verlag für Grundstoffindustrie, Leipzig 1975, p. 40-98).

Typically, the feed of the distillation column (X) is located at a position above 10% to 40%, more preferably above 15% to 30%, most preferably above 20% to 25% of the total number of theoretical stages of distillation column (X) and below 90% to 60%, more preferably below 85% to 70%, most preferably below 80% to 75% of the total number of theoretical stages of distillation column (X).

The heavy boilers exhibit a high degree of stickiness. Therefore it is advantageous to remove the heavy boilers first when starting to split the condensed substances from step II) into their components, before separating ethylbenzene from styrene.

Trays below the feed ensure easy separation of the heavy boilers from the other condensed substances from step II). The heavy boilers may be collected at the bottom of the distillation column (X) in a fraction (a2), and may thus be removed from the remaining mixture of condensed substances. At the same time, the light boilers may be concentrated at the head of the distillation column (X) in a fraction (a3) and thus may be removed from the product mixture as well.

The heavy boilers can be re-introduced to the initial de-polymerization process to increase the overall sustainability of the recycling process.

After having removed the heavy boilers in fraction (a2) and the light boilers in fraction (a3), the remaining fraction (a1) typically contains only styrenic monomers and other components that boil at a comparable temperature range, such as ethylbenzene. This fraction (a1) can then be drawn from the side of the distillation column (X), preferably using a liquid side draw or a vapor side draw, more preferably using a vapor side draw. The side draw is typically located at a position above 65% to 95%, preferably above 70% to 90%, more preferably above 75% to 85% and below 35% to 5%, preferably below 30% to 10%, more preferably below 25% to 15% of the total theoretical stages of distillation column (X).

It is advisable to operate the distillation column (X) at a bottom pressure of 150 mmHg to 400 mmHg, more preferably 200 mmHg to 350 mmHg, most preferably 250 mmHg to 300 mmHg, a head pressure of 100 to 300 mmHg, more preferably 150 mmHg to 250 mmHg, most preferably 180 mmHg to 220 mmHg, a bottom temperature of 200° C. to 300° C., more preferably 235° C. to 270° C., most preferably 240° C. to 265° C., and a head temperature of 40° C. to 80° C., more preferably 50° C. to 70° C., most preferably 53° C. to 67° C.

In a particularly preferred embodiment, the distillation column (X) is operated at a bottom pressure of 200 mmHg to 350 mmHg, a head pressure of 150 mmHg to 250 mmHg, a bottom temperature of 250° C. to 265° C. and a head temperature of 53° C. to 67° C.

It is advisable to use a polymerization inhibitor that is injected in the feed and reflux of the distillation column (X), to prevent the styrenic monomers from polymerizing. Examples for polymerization inhibitors are known from the literature, e.g. sterically hindered nitroxyl compounds, dinitrophenol-derivatives or 4-tert-butylcatechol (TBC).

Optional Step IV)

Optionally, in step IV), the mixture drawn from the position with the highest styrene concentration of the distillation column (X) from step III), if step III) is carried out, or otherwise the mixture of condensed substances from step (II) is fractionated in a distillation column (Y) with preferably at least 50, more preferably 60 to 95, most preferably 70 to 80 theoretical stages. It is advisable to use a packed column as distillation column (Y). In step IV) a fraction (b1) comprising styrenic monomers and any remaining substances with a higher boiling point than the styrenic monomers is preferably collected at the bottom of the distillation column (Y) and a fraction (b2) comprising ethylbenzene and any remaining substances with a lower boiling point than ethylbenzene is preferably collected at the head of the distillation column (Y).

Typically, the feed of the distillation column (Y) is located at a position above 20% to 80%, more preferably above 30% to 70%, most preferably above 40% to 60% of the total number of theoretical stages of distillation column (Y) and below 80% to 20%, more preferably below 70% to 30%, most preferably below 60% to 40% of the total number of theoretical stages of distillation column (Y).

In this way, ethylbenzene is removed from the styrenic monomers. Depending on the desired purity, the amount of theoretical stages can be chosen lower, but that will leave larger amounts of ethylbenzene in the final product. Depending on the polymerization inhibitor selected in the first distillation column, it might be useful to inject supplemental polymerization inhibitor in the second column as well.

The distillation column (Y) is preferably operated at a bottom pressure of 120 mmHg to 260 mmHg, more preferably 130 mmHg to 250 mmHg, most preferably 135 mmHg to 245 mmHg, a head pressure of 30 mmHg to 110 mmHg, more preferably 40 mmHg to 100 mmHg, most preferably 45 mmHg to 95 mmHg, a bottom temperature of 80° C. to 120° C., more preferably 90° C. to 110° C., most preferably 95° C. to 105° C., and a head temperature of 50° C. to 80° C., more preferably 55° C. to 75° C., most preferably 60° C. to 70° C. In a particularly preferred embodiment, the distillation column (Y) is operated at a bottom pressure of 135 mmHg to 245 mmHg, a head pressure of 45 mmHg to 95 mmHg, a bottom temperature of 92° C. to 110° C. and a head temperature of 56° C. to 74° C.

Optional Step V)

In this step, the fraction (b1) containing styrenic monomers collected at the bottom of the distillation column (Y) of step IV), which still may contain polymerization inhibitor, may be subjected to a third distillation process in a distillation column (Z), typically with more than 5 preferably more than 10, more preferably 50 to 180, most preferably 100 to 150 theoretical stages. In a particularly preferred embodiment, the distillation column (Z) contains 105 to 130 theoretical stages. The distillation column (Z) is preferably a packed column, a column with trays or a mixed column, more preferably a packed column.

Typically, the feed of the distillation column (Z) is located at a position above 20% to 80%, more preferably above 30% to 70%, most preferably above 40% to 60% of the total number of theoretical stages of distillation column (Z) and below 80% to 20%, more preferably below 70% to 30%, most preferably below 60% to 40% of the total number of theoretical stages of distillation column (Z).

This process step V) separates styrenic monomers from any remaining substances with a higher boiling point than the styrenic monomers, including the polymerization inhibitor and small amounts of polymer formed in spite of the polymerization inhibitor. The residue consisting of polymerization inhibitor and polymer, collected as fraction (c2) at the bottom of distillation column (Z) can be re-introduced to the initial depolymerization process to increase the overall sustainability of the recycling process even further.

The distillation column (Z) is typically operated at a bottom pressure of 100 mmHg to 350 mmHg, preferably 140 mmHg to 330 mmHg, more preferably 170 mmHg to 300 mmHg, most preferably 200 mmHg to 250 mmHg, a head pressure of 10 mmHg to 100 mmHg, preferably 20 mmHg to 90 mmHg, more preferably 30 mmHg to 80 mmHg, most preferably 45 mmHg to 65 mmHg, a bottom temperature of 80° C. to 150° C., preferably 100° C. to 140° C., more preferably 105° C. to 135° C., most preferably 110° C. to 125° C., and a head temperature of 45° C. to 100° C., preferably 50° C. to 80° C., more preferably 55° C. to 75° C., most preferably 60° C. to 70° C. In a particularly preferred embodiment, the distillation column (Z) is operated at a bottom pressure of 140 mmHg to 330 mmHg, a head pressure of 30 mmHg to 80 mmHg, a bottom temperature of 105° C. to 132° C. and a head temperature of 54° C. to 77° C.

The process described in this invention typically provides styrenic monomers with a purity of at least 40 wt-%, preferably at least 90 wt-%, most preferably at least 98 wt-% and allows for a re-polymerization of the styrenic monomers to polystyrene with sufficient quality for commercial applications.

By reversing the removal procedure of heavy boilers from the last step, as it is common in the industry, by introducing them into the pyrolysis reactor in step I), the process of the present invention provides an even better method for separating styrenic monomers from the polymer mixture (P).

The invention is further illustrated by the following examples and the claims.

EXAMPLES

Polymer mixtures (P) were heated in a flask to 350° to 450° C. This temperature is the average temperature of the polymer waste at the inner surface of the reactor wall during the reaction runtime. The results of depolymerization are summarized in Table 3.

DESCRIPTION OF THE DRAWING (FIG)

The drawings are schematic flow diagram of a particularly preferred embodiment of the process of the present invention, starting with step III).

It is an exemplary embodiment and is not meant to limit the invention. The drawing displays that the condensed substances (6), which are obtained after the pyrolysis step I) and the condensation step II), are introduced into a distillation column (1), which corresponds to distillation column (X). At the same time a first polymerization inhibitor (7) is introduced into the distillation column (1).

The light boilers (8), corresponding to fraction (a3), are partially removed from the head of the distillation column (1) and are partially condensed by a condenser (5) and reintroduced into the distillation column (1). The heavy boilers (9), corresponding to fraction (a2) are partially removed from the bottom of the distillation column (1) and are partially reboiled in a reboiler (4) and reintroduced into the distillation column (1).

The mixture comprising styrenic monomers (11) corresponding to fraction (a1) is withdrawn from distillation column (1) through a side draw (10) and introduced into a distillation column (2), corresponding to distillation column (Y). At the same time a second polymerization inhibitor (12) is introduced into the distillation column (2).

The fraction comprising ethylbenzene (13), corresponding to fraction (b2), is partially removed from the head of the distillation column (2) and is partially condensed by a condenser (5) and reintroduced into the distillation column (2). The fraction comprising styrenic monomers (14), corresponding to fraction (b1) is partially withdrawn from the bottom of the distillation column (2) and is partially reboiled in a reboiler (4) and reintroduced into the distillation column (2). The withdrawn portion of the fraction (14) is introduced into a distillation column (3), corresponding to distillation column (Z).

TABLE 3

Examples (E), reference Example (R) and comparative examples (C)

| | R1 | C2 | E2 | C3 | E3 | C4 | E4 | C5 | E5 |
|---|---|---|---|---|---|---|---|---|---|
| (P) | PS* | PS* + 10% Novodur P2H-AT** | PS* + 1% Novodur P2H-AT** | PS* + 2% PVC***** | PS* + 0.5% PVC***** | PS* + 10% PET*** | PS* + 2% PET*** | PS* + 20% Styrolux 3G55**** | PS* + 5% Styrolux 3G55**** |
| Main products | mono- and oligo-styrene | mono- and oligo-styrene + not identified products + black residue | mono- and oligo-styrene + few not identified products + low amount of black residue | trial stopped due to formation of HCl | mono- and oligo-styrene + lesser HCl formation depolymerisation can still be conducted | mono- and oligo-styrene + not identified products + black residue | mono- and oligo-styrene + not identified products + less black residue than in C4 | mono- and oligo-styrene + not identified products + black residue | mono- and oligo-styrene + not identified products + less black residue than in C5 |
| Styrene yield | 70% | <70% | <70% | n/a | <70% | <70% | <70% | <70% | <70% |
| Observation | — | >10 ppm HCN | <10 ppm HCN | HCl fume | | Black residue | Less black residue | Black residue | Less black residue |

*general purpose polystyrene (PS GPPS 158 N, INEOS Styrolution, Frankfurt)
**representative of a typical ABS (Novodur, INEOS Styrolution)
***polyethylene terephthalate
****representative of a typical styrene-butadiene copolymer (INEOS Styrolution)
*****polyvinyl chloride In the distillation column (3) a fraction comprising heavy boilers (15) corresponding to fraction (c2), is partially withdrawn from the bottom of the distillation column (3) and is partially re-boiled in a reboiler (4) and reintroduced into the distillation column (3).

The withdrawn part of fraction (15) is combined in a mixing utility (17) with the heavy boilers (9) withdrawn from the distillation column (1) to form a residue (18), which may be reintroduced into the pyrolysis reactor.

A second fraction (16), corresponding to fraction (c1), is partially removed from the head of the distillation column (3) and is partially condensed by a condenser (5) and reintroduced into the distillation column (3). The withdrawn fraction (16) is collected as the product, essentially consisting of styrenic monomers, e.g. styrene.

The invention claimed is:

1. A process for retrieving styrenic monomer from a polymer mixture (P),
   the polymer mixture (P) comprising:
   (A) 1 wt-% to 99.8 wt-%, related to the total weight of polymer mixture (P),
      of a styrenic polymer comprising:
      i. 70 wt-% to 100 wt-%, related to the total weight of (A), of repeating units derived from a styrenic monomer selected from styrene and alpha-methylstyrene;
      ii. 0 wt-% to 30 wt-%, related to the total weight of (A), of repeating units derived from dienes;
      iii. 0 wt-% to 2 wt-%, related to the total weight of (A), of repeating units derived from other radically co-polymerizable monomers;
   (B) 0.1 wt-% to 98.9 wt-%, related to the total weight of polymer mixture (P), of a mixture of polymers other than polymer (A);
   (C) 0.1 wt-% to 30 wt-%, related to the total weight of polymer mixture (P), of organic or inorganic polymer additives and auxiliaries; and optionally
   (D) 0 wt-% to 50 wt-%, related to the total weight of polymer mixture (P), of impurities such as, but not limited to, food waste, dirt, packaging residues or moisture,
   the process comprising the steps of:
   I) feeding the polymer mixture (P) into a pyrolysis zone of a pyrolysis reactor and subjecting it to a temperature of 300° C. to 650° C., measured as the average temperature of the polymer mixture (P) at the inner surface of the reactor wall during the reaction runtime, during which at least partial decomposition of the component (A) to styrenic monomers takes place, and a gas containing said styrenic monomers is formed;
   II) condensing the condensable substances including styrenic monomers from the gas formed in step I) at a cooling rate of more than 500° C./min (500 K/min);
   III) fractionating the condensed substances from step II) in a distillation column (X),
   wherein in step III),
   a fraction (a1) comprising styrenic monomers is withdrawn through a side outlet from the distillation column (X), at a position above 65% to 95% and below 35% to 5% of the total number of theoretical stages;
   a fraction (a2) comprising heavy boilers is collected at the bottom of the distillation column (X);
   a fraction (a3) comprising light boilers is collected at the head of the distillation column (X); and
   the distillation column (X) is operated at a bottom pressure of 200 hPa (150 mmHg) to 533 hPa (400 mmHg), a head pressure of 133 hPa (100 mmHg) to 400 hPa (300 mmHg), a bottom temperature of 200° C. to 300° C., and a head temperature of 40° C. to 80° C.

2. The process according to claim 1, wherein the polymer mixture (P) comprises 80 wt-% to 99.8 wt-%, related to the total weight of polymer mixture (P), of the styrenic polymer (A) and 0.1 wt-% to 19.9 wt-%, related to the total weight of polymer mixture (P) of the mixture of polymers (B).

3. The process according to claim 1, wherein a stabilizer or radical scavenger is added to the condensable substances in step II).

4. The process according to claim 1, further comprising the step
   IV) fractionating fraction (a1) obtained in step III) in a distillation column (Y).

5. The process according to claim 4, wherein in step IV) a fraction (b1) comprising styrenic monomers and components with a higher boiling point than the styrenic monomers is withdrawn from the bottom of the distillation column (Y) and a fraction (b2), comprising components with a lower boiling point than the styrenic monomers is withdrawn from the head of the distillation column (Y).

6. The process according to claim 4, wherein the distillation column (Y) is operated at a bottom pressure of 160 hPa (120 mmHg) to 347 hPa (260 mmHg), a head pressure of 40 hPa (30 mmHg) to 147 hPa (110 mmHg), a bottom temperature of 80° C. to 120° C., and a head temperature of 50° C. to 80° C.

7. The process according to claim 4, further comprising the step of:
   V) separating the fraction comprising styrenic monomers obtained in step IV) in a distillation column (Z), wherein
   a fraction (c1) comprising styrenic monomers is withdrawn from the head of the distillation column (Z); and
   a fraction (c2), comprising components with a higher boiling point than the styrenic monomers, is collected at the bottom of the distillation column (Z); wherein
   the distillation column (Z) is operated at a bottom pressure of 133 hPa (100 mmHg) to 467 hPa (350 mmHg), a head pressure of 13 hPa (10 mmHg) to 133 hPa (100 mmHg), a bottom temperature of 80° C. to 150° C., and a head temperature of 45° C. to 100° C.

8. The process according to claim 4, wherein the distillation column (Y) in step IV) comprises at least 50 theoretical stages.

9. The process according to claim 1, wherein the component (B) is a mixture of polymers selected from the group consisting of polyolefins; hydrogenated or non-hydrogenated ethylene-propylene-diene-rubber (EPDM); polyvinyl chloride (PVC); chlorinated polyvinyl chloride (c-PVC); polycarbonates; polyamides; and polyesters.

10. The process according to claim 1, wherein the component (B) contains
    iv. 0 wt-% to 1 wt-%, related to the total weight of polymer mixture (P), of PVC or c-PVC;
    v. 0 wt-% to 35 wt-%, related to the total weight of polymer mixture (P), of polyolefins, hydrogenated EPDM or non-hydrogenated EPDM;
    vi. 0 wt-% to 10 wt-%, related to the total weight of polymer mixture (P), of hydrogenated or non-hydrogenated styrene-butadiene copolymers comprising at least 15 wt-% butadiene based on the total weight of styrene-butadiene copolymer; and vii. 0 wt-% to 5 wt-%, related to the total weight of polymer mixture (P), of polyesters, polycarbonates or polyamides, provided that the amount of components selected from groups iv., v., vi. and vii. sums up to at least 0.1 wt-%, related to the total weight of polymer mixture (P).

11. The process according to claim 1, wherein the component (C) contains viii. 0 wt-% to 10 wt-%, related to the total weight of polymer mixture (P), of water;

ix. 0 wt-% to 1 wt-%, related to the total weight of polymer mixture (P), of halogenated substances;

x. 0 wt-% to 10 wt-%, related to the total weight of polymer mixture (P), of inorganic or organic dyes or pigments;

xi. 0 wt-% to 10 wt-%, related to the total weight of polymer mixture (P), of lubricants, waxes or amides of long chain organic acids;

xii. 0 wt-% to 5 wt-%, related to the total weight of polymer mixture (P), of emulsifiers or soaps;

xiii. 0 wt-% to 5 wt-%, related to the total weight of polymer mixture (P), of paper or cardboard;

xiv. 0 wt-% to 1 wt-%, related to the total weight of polymer mixture (P), of metals, metal oxides or metal salts;

xv. 0 wt-% to 10 wt-%, related to the total weight of polymer mixture (P), of further fillers; and xvi. 0 wt-% to 2 wt-%, related to the total weight of polymer mixture (P), of other additives such as UV stabilizers, HALS, hindered phenols, disulfite stabilizers, quenchers or absorbers, provided that the amount of components selected from groups viii., ix., x., xi., xii., xiii., xiv., xv., and xvi. sums up to at least 0.1 wt-%, related to the total weight of polymer mixture (P).

12. The process according to claim 1, wherein shear force and/or pressure are additionally applied to the polymer mixture (P) in the pyrolysis reactor in step I).

13. The process according to claim 1, wherein at least 3 theoretical stages are located below the position at which the condensed substances from step II) are introduced into the distillation column (X) in step III) and at least 17 theoretical stages are located above the position at which the condensed substances from step II) are introduced into the distillation column (X) in step III).

14. The process according to claim 1, wherein fraction (a2) collected at the bottom of the distillation column (X) in step III) is re-introduced into the pyrolysis zone of the pyrolysis reactor in step I).

15. The process according to claim 1, wherein the styrenic monomer retrieved by the process is styrene.

16. The process according to claim 1, wherein the distillation column (X) contains trays.

17. The process according to claim 7, wherein the distillation column (Z) contains more than 10 theoretical stages.

18. The process according to claim 7, wherein the distillation column (Z) is a packed column.

19. The process according to claim 1, wherein the distillation column (X) contains 20 to 40 theoretical stages.

20. The process according to claim 4, wherein the feed of the distillation column (Y) is located at a position above 20% to 80% of the total number of theoretical stages of distillation column (Y) and below 80% to 20% of the total number of theoretical stages of distillation column (Y).

* * * * *